United States Patent
Pilmanis

[11] Patent Number: 5,810,862
[45] Date of Patent: Sep. 22, 1998

[54] INSTRUMENT FOR THE INTRADERMAL INJECTION OF PIGMENTS

[76] Inventor: Paula Pilmanis, 27838 Pontevedra Dr., Rancho Palos Verdes, Calif. 90732

[21] Appl. No.: 246,284

[22] Filed: May 19, 1994

Related U.S. Application Data

[63] Continuation-in-part of Ser. No. 102,210, Aug. 5, 1993, abandoned.

[51] Int. Cl.[6] ........................... A61B 17/34
[52] U.S. Cl. ........................... 606/186; 81/9.22
[58] Field of Search .................. 606/186, 183; 81/9.22

[56] References Cited

U.S. PATENT DOCUMENTS 55,775  6/1866  Klee ............................ 606/186

FOREIGN PATENT DOCUMENTS 584297  2/1925  France ............................ 606/186
846767  8/1952  Germany .......................... 606/186
2234420  2/1991  United Kingdom ................. 81/9.22

*Primary Examiner*—Michael H. Thaler

[57] ABSTRACT

An instrument for the intradermal injection of liquid pigments which includes a needle assembly consisting of a number of needles, and a mass of solidified glue formed at one end of the needles to hold them in a predetermined relationship with one another and with their free ends projecting from the solidified glue at the opposite end. The instrument includes an elongated tubular barrel member and a tubular grip member which is mounted at the forward end of the barrel member in coaxial relationship. The grip member receives the needle assembly in a manner such that the free ends of the individual needles project through the forward end of the grip member. An appropriate resilient member is provided within the tubular member for biasing the needle assembly toward the forward end of the grip member so that the free ends of the needles will project out through the forward end of the grip member; or the needle assembly may be affixed to said grip member, for example, by a suitable adhesive.

2 Claims, 2 Drawing Sheets

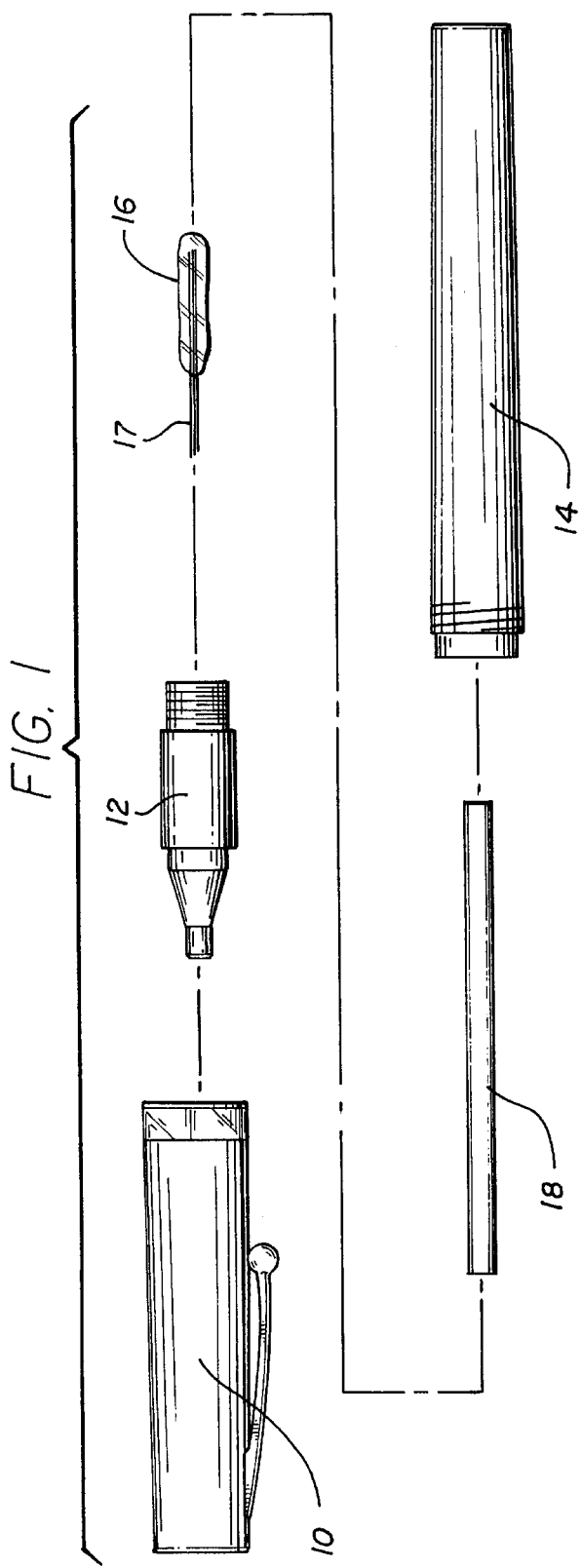
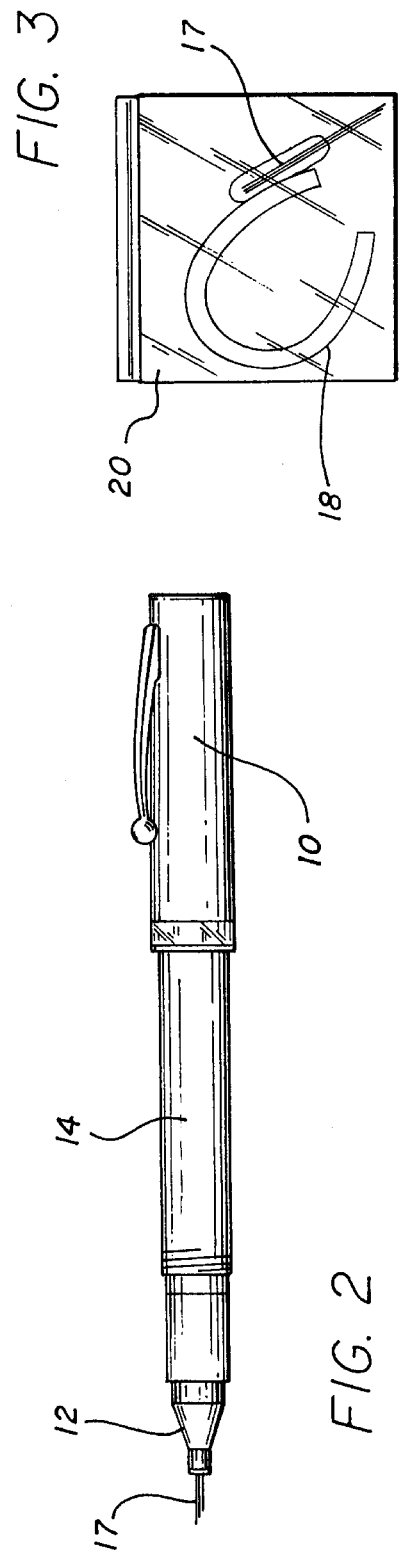
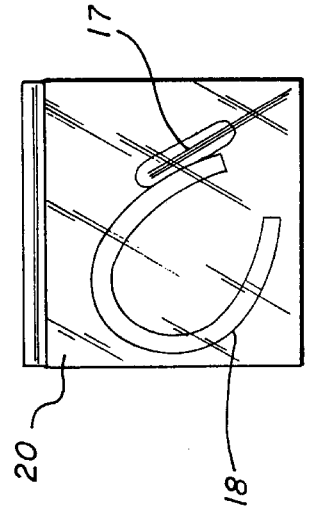

INSTRUMENT FOR THE INTRADERMAL INJECTION OF PIGMENTS

This is a Continuation-in-Part of application Ser. No. 08/102,210 filed Aug. 5, 1993 now abandoned.

BACKGROUND OF THE INVENTION

Various types of instruments are known for perforating the skin of a person with a needle, and for introducing a liquid pigment into the perforations. The ancient art of tattooing involves such a procedure to provide a permanent indicia or design under the skin tissue. More recently, such instruments have been used to introduce a liquid pigment into the eyelid of a person to provide a permanent eyeliner. The permanent eyeliner has a distinct advantage over the usual time consuming practice of applying eyeliner materials by a soft pencil or brush which requires a high degree of care both from the standpoint of obtaining an aesthetically pleasing appearance and from the standpoint of avoiding damage to the eye itself from the liquid pigment or from the instrument used to apply the liquid pigment to the eyelid.

Such instruments have also been used in procedures for eyebrow replacement or enhancement, and/or in corneal tattooing. In addition, instruments of this general type have been used by dermatologists for pigmentation at graft edges, for pigmentation in connection with hair transplants, as well as for pigmentation in connection with surgical reconstruction following mastectomy.

Intradermal pigment injection instruments of the type under consideration involve the use of needles either singularly or in an array mounted in a hand-held instrument, with the tips of the needles exposed through the end of the instrument for dipping into an appropriate pigment solution and for applying the pigment subdermally to the skin of the subject.

It is important from a sterilization standpoint, and to prevent the spread of disease, that the needles be changed after each use. Accordingly, the present invention in one embodiment is directed to an improved needle bar for holding a plurality of needles together in a desired relationship, and to an improved and simplified holder for the needle bar. The needle bar may be sold separately in sealed packages, and a new needle bar made in accordance with the teachings of the invention may be mounted in the grip of the improved holder of the invention quickly and easily. In a second embodiment the needle bar is permanently sealed in the grip and the entire instrument is made disposable.

BRIEF DESCRIPTION OF THE DRAWINGS

FIG. 1 is a detached representation of an intradermal injection instrument of the invention in accordance with one of its embodiments;

FIG. 2 is a representation of the instrument of FIG. 1, fully assembled and ready for use;

FIG. 3 is a representation of a package in which needle bars for the instrument of FIGS. 1 and 2 may be sold together with an appropriate resilient tube for biasing the needle bar to the forward end of the injection instrument.

DETAILED DESCRIPTION OF THE ILLUSTRATED EMBODIMENTS

Figure 4:
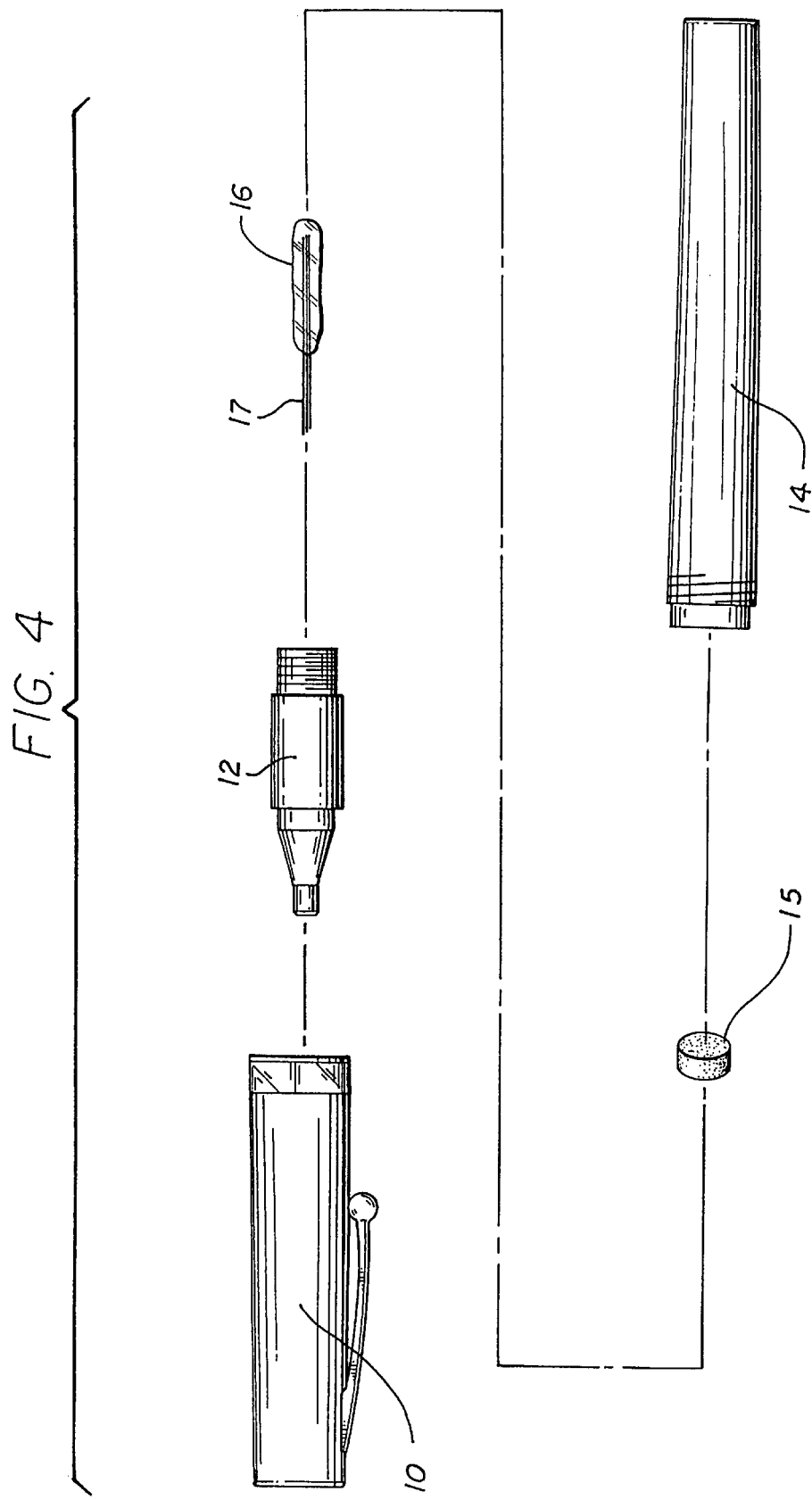
FIG. 4 is a detached representation of a second embodiment.

As shown in FIGS. 1 of the drawing, the intradermal injection instrument of the invention includes an elongated tubular cap 10 which when the instrument is not in use receives a tubular grip member 12 and a tubular barrel member 14 in coaxial relationship, with the grip member being threaded into one end of the barrel member, and with the barrel member being screwed into the end of the cap.

A needle bar 16, specially constructed in accordance with the invention, is received in the grip 12 and when the grip is threaded into the end of the barrel member an elongated resilient tube 18 serves to bias the needle bar 16 toward the forward end of the grip 12 so that an array of needles 17, which are contained in the needle bar 16, project through the end of the grip 12, as shown in FIG. 2. In FIG. 2, the cap 10 has been removed from the forward end of the instrument and mounted on the rear end so as to expose the needles 17 for actual use of the instrument.

As mentioned above, the needle bar 17 and the resilient member 18 may be sold separately in a plastic package 20, as shown in FIG. 3, so as to constitute refills for the instrument, and in order that a new needle bar may be inserted into the instrument each time the instrument is to be used on a different person. It is apparent that other types of resilient members, such as coiled springs, may be used.

In constructing the needle bar 16, a selected number of needles 17 are held between the thumb and forefinger and aligned so that the needles are positioned adjacent to one another in a planar array. The tips of the respective needles are displaced longitudinally with respect to one another, for example, at 40 degrees to the longitudinal axes of the needles. Three, four, six or more needles may be selected. Then, a coating of glue is formed on one end of the needle array by means of a glue gun to a length, for example, of ⅝ of an inch. Assuming the needles are approximately one inch long, the remaining ⅜ of an inch of the needles project through the end of the glue, which solidifies to form the needle bar 16.

To assemble the instrument, the grip 12 is unthreaded from the barrel 14, and the needle bar 16 is dropped into the grip, so that the free ends of the needles project through the forward end of the grip, as shown in FIG. 2. Then, the resilient tube 18 is dropped into the barrel 14, and the barrel is threaded to the grip 12 so that the needle bar 16 is biased by the tube toward the forward end of the grip, with the free ends of the needles 17 projecting through the grip.

When the instrument is not in use, the cap 10 is threaded onto the end of the barrel member 14 to enclose the grip 12 and needles 17. When the instrument is to be used, the cap 10 is removed and is slipped onto the rear end of the barrel 14, as shown in FIG. 2, and the cap is frictionally held on the barrel.

The second embodiment shown in FIG. 4 is generally similar to the embodiment of FIG. 1 and like elements have been designated by the same numbers. In the second embodiment, the resilient member 18 is eliminated. Instead, the needle bar 16 is dropped into the grip 12, as before, and then sealed in place by glue 15, or other appropriate material, which is injected into the rear end of the tubular grip 12.

The invention provides, therefore, a simple and inexpensive instrument for injecting pigments intradermally, and also discloses a simple and straightforward needle bar to be used within the instrument. The needle bar may be quickly and easily replaced for each use of the instrument to ensure sanitary conditions insofar as the subjects are concerned, or the instrument itself may be made to be disposable.

It will be appreciated that while particular embodiments of the invention have been shown and described, modifications may be made. It is intended in the claims to cover all such modifications which fall within the true spirit and scope of the invention.

I claim:

1. An instrument for the intradermal injection of liquid pigments including:

a needle bar consisting of a plurality of needles and a mass of solidified glue formed at one of the ends of the needles for holding the needles in a predetermined relationship with one another and with the other ends of the needles projecting from one end of the solidified glue;

an elongated tubular barrel member;

a tubular grip member mounted at one end of the barrel member in coaxial relationship therewith for coaxially receiving the needle bar with the ends of the individual needles projecting through the forward end of the grip member; and said needle bar is rigidly mounted in said grip member.

2. An instrument for the intradermal injection of liquid pigments including:

a needle bar consisting of a plurality of needles and a mass of solidified clue formed at one of the ends of the needles for holding the needles in a predetermined relationship with one another and with the other ends of the needles projecting from one end of the solidified glue;

an elongated tubular barrel member;

a tubular grip member mounted at one end of the barrel member in coaxial relationship therewith for coaxially receiving the needle bar with the ends of the individual needles projecting through the forward end of the grid member; and said needle bar is adhesively attached to said grip member.

* * * * *